United States Patent [19]

von Werner

[11] Patent Number: 5,051,535
[45] Date of Patent: Sep. 24, 1991

[54] PROCESS FOR THE PREPARATION OF EXTENSIVELY FLUORINATED ALIPHATIC HYDROCARBONS HAVING 1 OR 2 BROMINE OR CHLORINE ATOMS IN THE MOLECULE

[75] Inventor: Konrad Von Werner, Garching, Fed. Rep. of Germany

[73] Assignee: Hoechst Aktiengesellschaft, Frankfurt am Main, Fed. Rep. of Germany

[21] Appl. No.: 655,305

[22] Filed: Feb. 14, 1991

[30] Foreign Application Priority Data

Feb. 16, 1990 [DE] Fed. Rep. of Germany ....... 4004783

[51] Int. Cl.$^5$ ..................... C07C 17/20; C07C 41/00
[52] U.S. Cl. ..................................... 570/170; 568/684
[58] Field of Search ................ 570/170, 260; 568/684

[56] References Cited

U.S. PATENT DOCUMENTS

| | | |
|---|---|---|
| 2,678,953 | 5/1954 | Conly . |
| 2,875,253 | 2/1959 | Barnhart . |
| 3,972,953 | 8/1976 | Lyons ................................. 570/260 |
| 4,222,967 | 9/1980 | Boehm ............................... 570/170 |

FOREIGN PATENT DOCUMENTS 0194781  9/1986  European Pat. Off. .

OTHER PUBLICATIONS

Long, D. M. et al., "Is There a Time and Place for Radiopaque Fluorocarbons?", In Banks, *Preparation, Properties, and Industrial Applications of Organofluorine Compounds,* N.Y., Wiley, 1982, pp. 153–154.
Haszeldine, R. N., *J. Chem. Soc.*: 3761–3768, (1953).
Huang, B. et al., *Chem. Abs.*, 102:78312x, (1985).
Furutaka, Y. et al., *Chem. Abs.*, 104:88106p, (1986).

*Primary Examiner*—Alan Siegel

[57] ABSTRACT

A process is described for the preparation of the title compounds from the corresponding iodine-containing compounds by reaction with bromide or chloride ions present as salts, in a dipolar aprotic solvent, in the presence of a metal complex compound which contains chromium, nickel, cobalt or rhodium as the central atom and contains, per central atom, 1, 2 or 3 bromine or chlorine atoms and at least one additional phosphorus-containing ligand, at 20° to 140° C. Good yields are obtained in this way without the difficulties associated with the known procedure using elemental halogens at elevated temperatures. The compounds prepared can be used in the medical sector and as liquids resistant to high temperatures.

6 Claims, No Drawings

PROCESS FOR THE PREPARATION OF EXTENSIVELY FLUORINATED ALIPHATIC HYDROCARBONS HAVING 1 OR 2 BROMINE OR CHLORINE ATOMS IN THE MOLECULE

DESCRIPTION

The invention relates to a process for the preparation of extensively fluorinated aliphatic hydrocarbons having 1 or 2 bromine or chlorine atoms in the molecule, from the corresponding iodine-containing compounds.

It is known from U.S. Pat. No. 2,678,953 to obtain perfluoroalkyl bromides from the dry metal salts of perfluoroalkylcarboxylic acids by reaction with bromine, the conversion being increased by the use of visible light. The preferred silver salt is used in the single Example. This process is expensive because the perfluoroalkylcarboxylic acid must be prepared first, for example by the known reaction of perfluoroalkyl iodide with $SO_3$ or fuming sulfuric acid. The acid must then be converted to the metal salt and the latter dried. Furthermore, the reaction with bromine, which is poisonous and caustic, requires particular care and an increased expenditure on apparatus (safety measures, corrosion). Moreover, a $CF_2$ group of the perfluoroalkyl iodide is lost in the reaction chain.

Also, it is known from U.S. Pat. No. 2,875,253 to telomerize a lower hydrocarbon substituted with fluorine, bromine and, if appropriate, chlorine, as the telogen, with a fluorine-containing olefin with can additionally contain chlorine atoms, in the presence of a peroxidic polymerization promoter. As possible telogens, said patent mentions, inter alia, $CF_3Br$, $CF_2BrCl$, $CF_2Br_2$, $C_2F_5Br$, $C_2F_4BrCl$, $C_3F_6BrH$ and $C_3F_6Br_2$ and, among a large number of possible fluorine-containing olefins, tetrafluoroethylene. The reaction of these compounds would be expected to lead to extensively fluorinated alkyl bromides in the sense of the present invention, but no Examples are available which would make it possible to find out under what exact conditions and with what success the reaction can be carried out with tetrafluoro-ethylene. In the Examples, $CF_2=CFCl$ is always used as the fluorine-containing olefin.

In an essay by Long, Higgins, Mattrey, Mitten and Multer on radiopaque fluorinated hydrocarbons (R.E. Banks, "Preparation, Properties and Industrial Applications of Organofluorine Compounds", 1982, Ellis Horwood Ltd. Publishers/Chichester, pages 139 to 156), it is mentioned at the end of the explanations (bottom of page 154) that the perfluoro-n-hexyl bromide or perfluoroisoheptyl bromide used for the experiments was prepared by thermal bromination of the corresponding perfluoroalkyl iodides with elemental bromine, although no further information is given. Without doubt, the difficulties with apparatus when using bromine, which have already been mentioned above, increase when the reaction with this aggressive substance is carried out under thermal conditions, i.e. at higher temperatures.

R.N. Haszeldine, J. Chem. Soc., 1953, pages 3761 to 3768, and Huang Bingnan and Huang Weiyuan, Shanghai Inst. Org. Chem. Acad. Sinica, Huaxue Xuebao 42, pages 1106 to 1108 (C.A. 102; 78312x), 1984, describe the photochemical bromination of perfluoroalkyl iodides [Examples: $R_fI$ or $Cl(CF_2)_4I$] with bromine under UV radiation. $R_fBr$ or $Cl(CF_2)_4Br$ is obtained in very good yield after a reaction time of 168 or 50 hours respectively. However, this process is also expensive in terms of apparatus and energy.

Also, it is known from JP-Kokai No. 60-184033-A2, 1985 (C.A. 104; 88106p), to prepare $C_nF_{2n+1}Br$ (n=6 to 11) by reacting $C_nF_{2n+1}I$ with bromine in the presence of a radical-producing compound (for example azodiisobutyronitrile). $C_6F_{13}Br$ is obtained with a yield of 40% in this way.

Finally, it is known from EP No. 194 781 to prepare α, ω-dichloro- or α, ω-dibromo-perfluoroalkylene compounds by reacting the corresponding iodine compounds, which have been obtained by telomerization with tetrafluoroethylene, with elemental chlorine or bromine at temperatures of up to 180° C. In the last two processes mentioned, the use of the aggressive elemental halogens at higher temperatures again requires special measures in terms of apparatus.

It has now been found that the last process described can be improved by using certain metal complex compounds, it being possible to prepare not only extensively fluorinated alkyl bromides but also the corresponding chlorides with distinctly more favorable yields.

The novel process for the preparation of extensively fluorinated aliphatic hydrocarbons having 1 or 2 bromine or chlorine atoms in the molecule, from the corresponding extensively fluorinated aliphatic hydrocarbons having 1 or 2 primary or secondary iodine atoms in the molecule, by reacting 1 mol of bound iodine atom in the iodine compound with 1 to 4 mol of bromide or chloride ions present as salts with at least one of the following cations: Li, Na, K, Mg, Ca, Mn or substituted ammonium, in at least one dipolar aprotic solvent at 20° to 140° C. under normal atmospheric pressure or under the autogenous pressure of the reaction mixture, comprises carrying out the reaction in the presence of a metal complex compound which contains chromium, nickel, cobalt or rhodium as the central atom and contains, per central atom, 1, 2 or 3 bromine atoms in the case of the preparation of the extensively fluorinated aliphatic bromides, or 1, 2 or 3 chlorine atoms in the case of the preparation of the extensively fluorinated aliphatic chlorides, and, as additional ligands, at least one ligand of the following formulae:

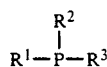

wherein $R^1$, $R^2$ and $R^3$, which are identical or different, are alkyl having 1 to 8 carbon atoms, alkoxy having 1 to carbon atoms, phenyl or phenoxy, which can be substituted by alkyl, alkoxy, phenyl or phenoxy groups and has 6 to 14 carbon atoms, or

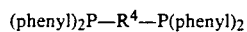

wherein $R^4$ is an alkylene radical having 1 to 6 carbon

Compounds of the following formula are suitable as starting materials for the process according to the invention:

in which X=H or a halogen atom and R is a linear or branched perfluorinated alkylene radical which contains to 16 carbon atoms when X=H, F or Cl and contains 3 to 16 carbon atoms when X =Br or I, and which can also contain an ether oxygen atom on at least 4 carbon atoms in each case. Examples of suitable compounds are

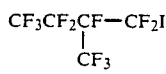

$CF_3CF_2CF_2OCF_2CF_2I$

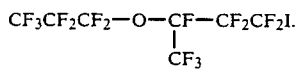

It is preferred to use compounds of formula (I) which contain no ether oxygen atoms; other preferred compounds are those in which X=I and especially those in which X is F and R is a perfluorinated alkylene radical which is either linear or branched by a methyl group in the ω-position to the iodine atom. Compounds of formula (I) in which the radical R contains more than 16 carbon atoms generally give longer reaction times and often poorer yields; they are also less easy to use as a rule. Because of their ease of use, preferred compounds of formula (I) are those in which R is an alkylene radical having 2 to 12 and especially 6 to 8 carbon atoms. In place of the compounds of formula (I), it is also possible to use compounds which contain secondary iodine atoms instead of the primary iodine atom(s). A primary iodine atom is understood here as meaning an iodine atom bonded to a carbon atom which in turn has either one bond or no bond at all to another carbon atom, while a secondary iodine atom is an iodine atom bonded to a carbon atom which in turn has a single bond to each of two other carbon atoms. It is also possible to use mixtures of compounds of formula (I) which contain different substituents X and/or different perfluorinated alkylene radicals R, as well as mixtures of compounds containing primary and secondary iodine atoms.

According to the invention, 1 mol of bound iodine atom in the compound of formula (I), or in a corresponding compound containing secondary iodine atoms, is reacted with 1 to 4 mol of bromide ions or chloride ions which can be present as salts with various cations. If less than 1 mol of bromide ion or chloride ion is used per mol of iodine atom in the compound of formula (I) or in a corresponding compound containing secondary iodine atoms, poorer yields are obtained. In principle, it is possible to use more than 4 mol of bromide or chloride ions per mol of iodine atom, but this is not generally found to improve the yield and is therefore an unnecessary expense. It is preferred to use 1.2 to 2 mol of bromide or chloride ions per mol of iodine atom in the compound of formula (I) or in a corresponding compound containing secondary iodine atoms.

The bromide or chloride ions can be present as salts of substituted ammonium; examples of possible substituents on the nitrogen of the ammonium are alkyl groups having 1 to 20 carbon atoms and/or hydroxyalkyl groups having 2 to 4 carbon atoms, the total number of carbon atoms in the substituted ammonium not exceeding 40. The bromide or chloride ions can also be present as salts with at least one of the following cations: sodium, potassium, magnesium or calcium. It is preferred to use manganese or tetraalkylammonium bromides or chlorides Particularly good results are obtained when at least some of the bromide or chloride ions are present as lithium salts. It is also possible to use mixtures of salts which contain either the bromide ion or the chloride ion, but different cations.

According to the invention, the reaction of the compounds of formula (I), or corresponding compounds containing secondary iodine atoms, with the salts containing bromide or chloride ions is carried out in the presence of a metal complex compound which contains chromium, nickel, cobalt or rhodium as the central atom and contains, per central atom, 1, 2 or 3 bromine atoms in the case of the preparation of extensively fluorinated aliphatic bromides, or 1, 2 or 3 chlorine atoms in the case of the preparation of extensively fluorinated aliphatic chlorides. It is preferred to use a metal complex compound which contains nickel as the central atom and has 2 bromine atoms or 2 chlorine atoms The metal complex compound should contain, as additional ligands, at least one ligand of the following formulae

wherein $R^1$, $R^2$ and $R^3$, which are identical or different, are alkyl having 1 to 8 carbon atoms, alkoxy having 1 to 8 carbon atoms, phenyl or phenoxy, which can be substituted by alkyl, alkoxy, phenyl or phenoxy groups and has 6 to 14 carbon atoms, or

wherein $R^4$ is an alkylene radical having 1 to 6 carbon atoms. Because of their good action and favorable accessibility, preferred metal complex compounds are those carrying at least one ligand of formula (II) in which $R^1$, $R^2$ and $R^3$ are identical and are an alkyl radical having 4 to 8 carbon atoms, an alkoxy radical having 2 to 4 carbon atoms, a phenyl radical or a phenoxy radical. Other preferred metal complex compounds are those carrying at least one ligand of formula (III) in which $R^4$ is an alkylene radical having 2 to 4 carbon atoms.

Apart from the ligands of formula (II) or (III), the metal complex compound can also contain other ligands known for such compounds, for example CO, NO, $NZ_3$, $AsZ_3$ and $SbZ_3$, wherein Z is an alkyl radical having 1 to 6 carbon atoms or an aryl or alkylaryl radical having 6 to 2 carbon atoms, as well as heterocyclic compounds having nitrogen atoms in the ring, such as pyridine. The metal complex compound can also be present as an anion which forms a salt-like compound with a suitable cation, for example an alkali metal or alkaline earth metal.

Examples of suitable metal complex compounds are:
$[(C_4H_9)_3P]_2NiBr_2$; $[(C_2H_5O)_3P]_2 NiBr_2$;
$[(phenyl)_3P]_2NiCl_2$; $[(phenyl)_3P]_2NiBr_2$;
$[(phenyl)_3P]_2Ni_2Br_4$; $Li[(phenyl)_3PNiBr_3]$;
$[(p-tolyl)_3P]_2NiCl_2$; $[(phenyl)_3P]_2Ni(NO)Br$;
$[(phenyl)_2P-(CH_2)_2-P(phenyl)_2]NiCl_2$;
$[(phenyl)_2P-(CH_2)_4-P(phenyl)_2]NiBr_2$;
$[(phenoxy)_3P]_2NiBr_2$; $[(phenyl)_3P]_2CoCl_2$;
$[(p-tolyl)_3P]_2CoBr_2$;
$[(phenyl)_2P-(CH_2)_2-P(phenyl)_2]CoBr_2$;
$[(phenyl)_3P]_2Rh(CO)Br$; $[(phenyl)_3P]_4CrBr_2$.

Heterogeneous metal complex compounds in which the metal complex is contained in a polymer chain are also suitable, an example being

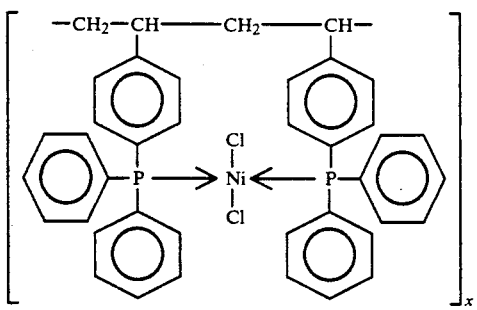

The preparation of said metal complex compounds is known —see, for example, Gmelins Handbuch der anorganischen Chemie (Gmelins Handbook of Inorganic Chemistry), 8th edition, Verlag Chemie/Weinheim, FR Germany, volume 52, part C, page 19; volume 57, part C, instalment 2, page 1031 et seq., and volume 64 (Rh), supplement volume B1, page 92. The metal complex compounds can be prepared as such before they are used, or they can also be prepared in situ, advantageously in some cases, by adding the starting materials to the reaction mixture, which already contains a compound of formula (I), or a corresponding compound containing secondary iodine atoms, and a bromide or chloride salt.

0.001 to 1 mol of metal complex compound is used per mol of bound iodine atom in the iodine compound. Below 0.001 mol of metal complex compound, the desired increase in yield is generally no longer found, and above 1 mol, there is generally no further improvement in the inventive effect within the framework of the process according to the invention. However, it is also possible to use more than 1 mol, for example 1.1 to 2 mol, of metal complex compound per mol of iodine atoms in the compound of formula (I), or in a corresponding compound containing secondary iodine atoms, it no longer being necessary to add bromide ions or chloride ions present as salts. Nevertheless, this process is relatively expensive, so it is only worth using in special cases, if at all. It is preferred to use 0.02 to 0.2 mol of metal complex compound per mol of iodine atoms in the iodine-containing compound.

The reaction according to the invention is carried out in a dipolar aprotic solvent, 0.5 to 50 cm³ of solvent being used per g of compound of formula (I) or of a corresponding compound containing secondary iodine atoms. These limits are not critical; for example, it is also possible to use more than 50 cm³ of solvent per g of iodine-containing compound, although it is generally sufficient to choose an amount of solvent within said range; it is preferred to use 1 to 20 cm³ of solvent per g of iodine-containing compound. Examples of suitable dipolar aprotic solvents are dioxane, acetone, alkyl carboxylates such as ethyl acetate, dialkyl ethers of glycol and polyglycols, such as tetraethylene glycol dimethyl ether, methylene chloride and N,N-dimethylformamide. Particularly good results are obtained if the reaction according to the invention is carried out in at least one of the following solvents: tetrahydrofuran, N,N-dimethylacetamide, acetonitrile, benzonitrile and nitrobenzene. Mixtures of different dipolar aprotic solvents can also be used. It is convenient to use a solvent or solvent mixture which, under normal atmospheric pressure, boils at least 10° C., advantageously at least 20° C., above or below the extensively fluorinated bromine- or chlorine-containing compound to be prepared.

The reaction described above is carried out at a temperature of 20 to 140° C and conveniently takes place under normal atmospheric pressure or under the autogenous pressure of the reaction mixture. As a rule, the use of higher pressures is not necessary and represents an unnecessary expense. Below 20° C., the reaction generally proceeds too slowly; above 140° C., the formation of undesired by-products is found to increase. The reaction is preferably carried out at temperatures of 50° to 90° C.

The reaction time depends on the temperature and starting materials used and is generally 1 to 20 hours; longer reaction times are possible, but the additional effect observed cannot usually be justified by the increasingly poor space-time yields. Good results are often obtained with a reaction time of 2 to 8 hours.

The reaction according to the invention is advantageously carried out in an inert gas, for example nitrogen or argon, with the exclusion of oxygen.

When the reaction has ended, the mixture can be worked up in various ways, for example by distilling off all the volatile components, including the solvents, under reduced pressure, at bottom temperatures up to a maximum of about 100° C. The distillate obtained in this way is then separated by fractional distillation into the components (extensively fluorinated chlorine- or bromine-containing compound prepared, unconverted iodine-containing compound and solvents), it being possible for the last two to be re-used. In a preferred embodiment, the amount of extensively fluorinated iodine-containing compound in the crude distillate prepared is determined by analysis and the process according to the invention is repeated without the addition of solvents or with the addition of only a small amount of solvents, after which all the volatile constituents are again distilled off and then separated by fractional distillation.

Another possible way of working up the reaction mixture is to dilute it with a dialkyl ether having 2 to 8 carbon atoms in the alkyl groups, for example diethyl ether, or with diallyl ether, methylene chloride or 1,1,2-trichloro-1,2,2-trifluoroethane (F113), the volume used being at least twice that of the extensively fluorinated iodine-containing compound used. The mixture is then thoroughly mixed with water, conveniently at a temperature of 18° to 50° C., preferably 20° to 30° C., the aqueous phase is separated from the organic phase and the latter is washed with water again, filtered, dried and then either fractionally distilled immediately or, as described above, reacted again according to the invention and then fractionally distilled.

The metal cation contained as the central atom in the metal complex compound can be recovered from the residue remaining after working-up, and re-used after regeneration of the complex compound before addition or in situ in the reaction mixture.

The extensively fluorinated aliphatic hydrocarbons containing 1 or 2 bromine atoms, prepared by the process according to the invention, can be used in the medical sector, for instance as contrast media in examinations with X-rays or with ultrasound, for example for visualizing tumors, for organ perfusion and in aqueous emulsion as blood substitutes. The extensively fluorinated aliphatic hydrocarbons containing 1 or 2 bromine or chlorine atoms can also be used as liquids inert at high temperatures and as contrast media for $^{19}F$ NMR analysis and tomography.

As already mentioned at the outset, the process according to the invention makes it possible to work in inexpensive apparatuses without corrosion problems or particular safety measures. The novel process occasionally gives rise to smaller amounts of by-products, which can be isolated in conventional manner and have a variety of uses. The compounds which contain a hydrogen atom in place of the iodine atom can be used for example as heat transfer fluids.

The following Examples will serve to illustrate the invention in greater detail.

The analysis results were obtained as follows: A sample is examined by $^{19}F$ NMR after the addition of $CDCl_3$. For $R_FY$ compounds (Y = I, Br, Cl), the chemical shifts of the fluorine atoms in the a- and b-positions to Y are distinguished in the typical way: Compared with $R_FI$, the a- and b-resonances of $R_FBr$ are shifted to a higher field and those of $R_FCl$ to an even higher field. A second sample is examined by gas chromatography. This is done using a column containing 10% of UCCW (a polyvinylmethylsilicone from Hewlett Packard) on Embacel ($SiO_2$ of large surface area, 60 to 100 mesh particles). The carrier gas is helium and a thermal conductivity detector is used. The assignment of the gas chromatography peaks is substantiated by reference gas chromatography with pure substances. The results obtained from $^{19}F$ NMR and gas chromatography are usually in good agreement. The values indicated below (in mol%) are the mean values from NMR and gas chromatography data.

Examples 1 to 14 are carried out as follows

The chemicals used for the various reactions are first dried carefully. The perfluoroalkyl iodide used has a purity of at least 99.5%; it is treated with copper powder to remove any traces of free halogen which may be present, and is stored in a brown bottle in the dark.

A four-necked flask with a capacity of 50 $cm^3$, equipped with a condenser, a gas inlet tube and a contact thermometer, is evacuated and dried with a heavy-duty hot air blower. After the vacuum has been let down with dry argon, a valve filled with silicone oil is fixed to the condenser, a magnetic stirrer bar coated with polytetrafluoroethylene is introduced into the flask and the flask is placed in a heating bath.

The amount of solvent indicated in the Table below is then introduced into the flask and saturated with argon.

With stirring, the reactants listed in the Table are then added, in finely divided form if they are solids, and the mixture is heated to the temperature shown in the Table and kept at this temperature for the indicated time. The reaction mixture is then cooled to 20° C. and 4 $cm^3$ of diethyl ether are added first, followed by 20 $cm^3$ of water. The contents of the flask are stirred throughout this time. The stirring is then stopped and the mixture separates into an aqueous layer and an ether-containing layer. The latter is separated off, extracted three times by shaking with water and dried, and one sample is examined by $^{19}F$ NMR and one by gas chromatography. The mean values from both the analytical methods are indicated in the Table below.

---

I = $(Ph_3P)_2NiBr_2$  Ph = phenyl
II = $[(C_4H_9)_3P]_2NiBr_2$
III = $[(C_2H_5O)_3P]_2NiBr_2$
IV = $[(PhO)_3P]_2NiBr_2$
V = $(Ph_3P)_2NiCl_2$
VI = $(Ph_3P)_2Rh(CO)Br$
VII = $[Ph_2P(CH_2)_2PPh_2]NiBr_2$
DMA = dimethylacetamide

---

(1) = + 1 mmol of cetyltrimethylammonium bromide
(2) 49.8 mol % of $I(CF_2)_4Br$ + 9.5 mol % of $Br(CF_2)_4Br$ $C_6F_{13}Br$ is prepared in Examples 1 to 5 and 9, $C_8F_{17}Br$ in Examples 6, 8, 10, 11 and 13, $C_8F_{17}Cl$ in Example 7 and $CF_2CF_2CF_2OCF(CF_3)CF_2Br$ in Example 14.

"H-containing compound" is to be understood in each case as meaning the compound which contains a hydrogen atom in place of the iodine atom present in the starting material.

TABLE

| Example n# | Iodine-containing compound (a) | Amount of (a) mmol | Br⁻- or Cl⁻- containing salt (b) | Amount of (b) mmol | Metal complex (c) | Amount of (c) mmol | Solvent | Amount $cm^3$ | Mol of Br⁻ or Cl⁻ per mol of iodine in (a) |
|---|---|---|---|---|---|---|---|---|---|
| 1 | $C_6F_{13}I$ | 2 | LiBr | 2 | I | 2 | $CH_3CN$ | 10 | 1 |
| 2 | $C_6F_{13}I$ | 2 | NaBr | 2 | I | 2 | $CH_3CN$ | 10 | 1 |
| 3 | $C_6F_{13}I$ | 2 | LiBr | 2 | II | 2 | $CH_3CN$ | 10 | 1 |
| 4 | $C_6F_{13}I$ | 2 | LiBr | 2 | III | 2 | $CH_3CN$ | 10 | 1 |
| 5 | $C_6F_{13}I$ | 2 | LiBr | 2 | IV | 2 | $CH_3CN$ | 10 | 1 |
| 6 | $C_8F_{17}I$ | 2 | LiBr | 2 | II | 2 | DMA | 10 | 1 |
| 7 | $C_8F_{17}I$ | 2 | LiCl | 2 | V | 2 | $C_6H_5NO_2$ | 10 | 1 |
| 8 | $C_8F_{17}I$ | 5 | LiBr | 7.5 | I | 0.25 | $CH_3CN$ | 10 | 1.5 |
| 9 | $C_6F_{13}I$ | 5 | LiBr$^{(1)}$ | 5 + 1 | I | 1 | $CH_3CN$ | 10 | 1.2 |
| 10 | $C_8F_{17}I$ | 5 | $MnBr_2$ | 3.75 | I | 0.5 | $CH_3CN$ | 10 | 1.5 |
| 11 | $C_8F_{17}I$ | 5 | $MgBr_2$ | 3.75 | I | 0.5 | $CH_3CN$ | 10 | 1.5 |
| 12 | $I(CF_2)_4I$ | 2 | LiBr | 6 | I | 0.4 | $CH_3CN$ | 20 | 1.5 |
| 13 | $C_8F_{17}I$ | 1 | LiBr | 1 | VI | 1 | $CH_3CN$ | 5 | 1 |
| 14 | $C_3F_7OCF(CF_2)_2I$<br>      $\vert$<br>      $CF_3$ | 5 | LiBr | 7.5 | VII | 0.5 | DMA | 10 | 1.5 |

| Example n# | Mol of (c) per mol of iodine in (a) | $cm^3$ of solvent per g of (a) | Temperature #C | Time h | Br- or Cl-containing compound prepared | Mean analytical values mol % Unconverted iodine-containing compound | H-containing compound | Undefined residue |
|---|---|---|---|---|---|---|---|---|
| 1 | 1 | 11.2 | 80 | 7 | 85.9 | — | — | — |
| 2 | 1 | 11.2 | 80 | 7 | 91 | 9 | — | — |
| 3 | 1 | 11.2 | 70 | 6 | 83 | 16 | 1 | — |
| 4 | 1 | 11.2 | 80 | 7 | 70.7 | 22.1 | 7.2 | — |
| 5 | 1 | 11.2 | 80 | 7 | 89.7 | 10.3 | — | — |
| 6 | 1 | 9.2 | 60 | 5 | 64 | 31 | 5 | — |
| 7 | 1 | 9.2 | 70 | 7 | 78 | 22 | — | — |

TABLE-continued

| | | | | | | | | |
|---|---|---|---|---|---|---|---|---|
| 8 | 0.5 | 3.7 | 80 | 6.5 | 75 | 24.5 | — | 0.5 |
| 9 | 0.2 | 4.5 | 80 | 2 | 47.7 | 51.6 | — | 0.7 |
| 10 | 0.1 | 3.7 | 80 | 7 | 54.5 | 42.5 | — | 3.0 |
| 11 | 0.1 | 3.7 | 80 | 7 | 61.5 | 38.5 | — | — |
| 12 | 0.1 | 22 | 80 | 7 | (2) | 40.7 | — | — |
| 13 | 1 | 9.2 | 80 | 7 | 32.6 | 58.6 | — | 8.8 |
| 14 | 0.1 | 3.9 | 60 | 7 | 68 | 30 | 1.5 | 0.5 |

What is claimed is:

1. A process for the preparation of extensively fluorinated aliphatic hydrocarbons having 1 or 2 bromine or chlorine atoms in the molecule, from the corresponding extensively fluorinated aliphatic hydrocarbons having 1 or 2 primary or 1 or 2 secondary iodine atoms in the molecule, by reacting 1 mol of bound iodine atom in the iodine compound with 1 to 4 mol of bromide or chloride ions present as salts with at least one of the following cations: Li, Na, K, Mg, Ca, Mn or substituted ammonium, in at least one dipolar aprotic solvent at 20° to 140° C. under normal atmospheric pressure or under the autogenous pressure of the reaction mixture, which comprises carrying out the reaction in the presence of a metal complex compound which contains chromium, nickel, cobalt or rhodium as the central atom and contains, per central atom, 1, 2 or 3 bromine atoms in the case of the preparation of the extensively fluorinated aliphatic bromides, or 1, 2 or 3 chlorine atoms in the case of the preparation of the extensively fluorinated aliphatic chlorides, and, as additional ligands, at least one ligand of the following formulae:

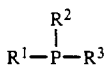

wherein $R^1$, $R^2$ and $R^3$, which are identical or different, are alkyl having 1 to 8 carbon atoms, alkoxy having 1 to 8 carbon atoms, phenyl or phenoxy, which can be substituted by alkyl, alkoxy, phenyl or phenoxy groups and has 6 to 14 carbon atoms, or

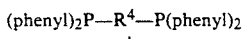

wherein R is an alkylene radical having 1 to 6 carbon atoms.

2. A process as claimed in claim 1, wherein perfluoroalkyl iodides having 2 to 12 carbon atoms are used for the reaction to prepare the perfluoroalkyl bromides or the perfluoroalkyl chlorides.

3. A process as claimed in claim 1, wherein the reaction is carried out in the presence of a metal complex compound of nickel which has 2 bromine atoms in the case of the preparation of the extensively fluorinated aliphatic bromides, or 2 chlorine atoms in the case of the preparation of the extensively fluorinated aliphatic chlorides.

4. A process as claimed in claim 1, wherein the reaction is carried out in at least one of the following solvents: tetrahydrofuran, N,N-dimethylacetamide, acetonitrile, benzonitrile and nitrobenzene.

5. A process as claimed in claim 1, wherein the reaction is carried out at 50 to 90° C.

6. A process as claimed in claim 1, wherein the bromide ions or the chloride ions are present as lithium salts.

* * * * *